(12) United States Patent
Klein

(10) Patent No.: US 6,605,107 B1
(45) Date of Patent: Aug. 12, 2003

(54) RADIALLY EXPANSIBLE VESSEL SCAFFOLDS MOUNTED OVER BALLOONS

(75) Inventor: Enrique J. Klein, Los Altos, CA (US)

(73) Assignee: Avantec Vascular Corporation, Sunnyvale, CA (US)

(*) Notice: Subject to any disclaimer, the term of this patent is extended or adjusted under 35 U.S.C. 154(b) by 0 days.

(21) Appl. No.: 09/687,610

(22) Filed: Oct. 11, 2000

Related U.S. Application Data

(60) Division of application No. 08/968,319, filed on Nov. 12, 1997, which is a continuation-in-part of application No. PCT/US96/07942, filed on May 29, 1996, which is a continuation-in-part of application No. 08/463,166, filed on Jun. 5, 1995, now Pat. No. 5,593,442.

(60) Provisional application No. 60/060,938, filed on Oct. 23, 1997.

(51) Int. Cl.[7] .......................... A61F 2/06; A61M 29/00

(52) U.S. Cl. ..................... 623/1.11; 606/194; 606/192

(58) Field of Search ................. 623/1.11, 1.24, 623/1.26; 606/198, 194, 192, 195

(56) References Cited

U.S. PATENT DOCUMENTS

| | | | |
|---|---|---|---|
| 4,564,014 A | * | 1/1986 | Fogarty et al. ............. 128/344 |
| 4,733,665 A | * | 3/1988 | Palmaz ...................... 128/343 |
| 4,776,337 A | | 10/1988 | Palmaz |
| 5,064,435 A | | 11/1991 | Porter |
| 5,087,247 A | | 2/1992 | Horn et al. |
| 5,102,417 A | | 4/1992 | Palmz |
| 5,104,404 A | | 4/1992 | Wolf |
| 5,135,536 A | | 8/1992 | Hillstead |
| 5,195,984 A | | 3/1993 | Schatz |
| 5,228,441 A | | 7/1993 | Lundquist |
| 5,243,167 A | | 9/1993 | Lundquist et al. |
| 5,282,824 A | | 2/1994 | Gianturco |
| 5,328,467 A | | 7/1994 | Edwards et al. |
| 5,329,923 A | | 7/1994 | Lundquist |

(List continued on next page.)

FOREIGN PATENT DOCUMENTS

| | | |
|---|---|---|
| CA | 2079944 | 4/1993 |
| EP | 0481365 | 4/1992 |
| EP | 0540290 | 5/1993 |
| EP | 0662307 | 7/1995 |
| EP | 0750890 | 1/1997 |
| WO | WO 92/06734 | 4/1992 |

OTHER PUBLICATIONS

Hodgson, "Focal stenting: Does it make sense?" Catheterization and Cardiovascular Diagnosis (1997) 42:137.

Lowe et al., "New balloon expandable stent for bifurcation lesions" Catherization and Cardiovascular Diagnosis (1997) 42:235–236.

(List continued on next page.)

Primary Examiner—Corrine McDermott
Assistant Examiner—Alvin Stewart
(74) Attorney, Agent, or Firm—Townsend and Townsend and Crew LLP; Soodabeh Tronson

(57) ABSTRACT

The present invention provides improved prostheses and methods for their endolumenal placement within body lumens, particularly blood vessels. In one embodiment, the prosthesis of the present invention consists a plurality of radially expansible rings having, a plurality of beams connecting axially remote points on adjacent rings, and a plurality of expansion joints connecting axially proximate points on adjacent rings. The beams maintain the remote points at a fixed distance when the prosthesis is radially expanded and the expansion joints allow for relative movement of the proximate points during delivery of the prosthesis. The combination of the beams and expansion joints minimizes the risk of injury to the body lumen during delivery of the prosthesis to a target site and provides improved tracking capabilities.

8 Claims, 18 Drawing Sheets

U.S. PATENT DOCUMENTS

| | | | |
|---|---|---|---|
| 5,334,145 A | | 8/1994 | Lundquist et al. |
| 5,354,308 A | | 10/1994 | Simon et al. |
| 5,383,892 A | | 1/1995 | Cardon et al. |
| 5,443,498 A | | 8/1995 | Fontaine |
| 5,449,373 A | | 9/1995 | Pinchasik et al. |
| 5,514,154 A | | 5/1996 | Lau et al. |
| 5,578,149 A | | 11/1996 | DeScheerder et al. |
| 5,591,197 A | | 1/1997 | Orth et al. |
| 5,591,230 A | | 1/1997 | Horn et al. |
| 5,593,442 A | | 1/1997 | Klein |
| 5,607,467 A | * | 3/1997 | Froix ................. 623/1.11 |
| 5,634,928 A | * | 6/1997 | Fischell et al. ............. 606/108 |
| 5,643,279 A | * | 7/1997 | Trotta ................. 606/198 |
| 5,669,932 A | * | 9/1997 | Fischell et al. ............. 606/198 |
| 5,693,066 A | * | 12/1997 | Rupp et al. ................. 606/198 |
| 5,741,327 A | | 4/1998 | Frantzen |
| 5,755,776 A | | 5/1998 | Al Saadon |
| 5,755,781 A | | 5/1998 | Jayaraman |
| 5,766,238 A | | 6/1998 | Lau et al. |
| 5,824,045 A | * | 10/1998 | Alt ................. 623/1.15 |
| 5,893,868 A | * | 4/1999 | Hanson et al. ............. 606/198 |
| 5,964,798 A | | 10/1999 | Imran |
| 5,980,531 A | * | 11/1999 | Goodin et al. ............. 606/108 |
| 5,980,532 A | * | 11/1999 | Wang ................. 606/198 |
| 6,036,725 A | | 3/2000 | Avellanet |
| 6,068,656 A | | 5/2000 | Von Oepen |
| 6,099,561 A | | 8/2000 | Alt |

OTHER PUBLICATIONS

Mudra et al., "One balloon approach for otimized Palmaz–Schatz Stent Implantation: The MUSCAT Trial" Catheterization and Cardiovascular Diagnosis (1997) 42:130–136.

Product Brochure for "Freedom™ Coronary Stent" by Global Therapeutics, Inc., 2150 West 6th Avenue, Broomfield, CO, 80020 USA, 3 pages total.

Product Brochure for "V–Flex™ Coronary Stent" by Global Therapeutics, Inc., 2150 West 6th Avenue, Broomfield, CO, 80020 USA, 2 pages total.

Product Brochure for "Tapered USCI Sprint™ Over-–the–wire Balloon Dilation Catheter with Banka™ Tapered Balloon" by Bard, 1200 Technology Park Drive, Billerica, MA, 01821–7025 USA, 2 pages total.

Product Brochure for "Jostent® Plus and Jostent® Flex" by Jomed International AB, Drottninggatatn 94, S–252 21 Helsingborg, Sweden, 4 pages total.

Product Brochure for "The Cat™" by CardioVascular Dynamics, Inc., 13844 Alton Parkway, Suite 140, Irvine, CA 92718 USA, 2 pages total.

Product Brochure for "Paragon Coronary Stent™" by Progressive Angioplasty Systems Canada Inc., 5250 Ferrier Street, Suite 406, Montreal, Quebec, H4P 1L4 Canada, 2 pages total.

Product Brochure for "FocusStent™" by CardioVascular Dynamics, Inc., 13844 Alton Parkway, Suite 140, Irvine, CA 92718 USA, 2 pages total.

* cited by examiner

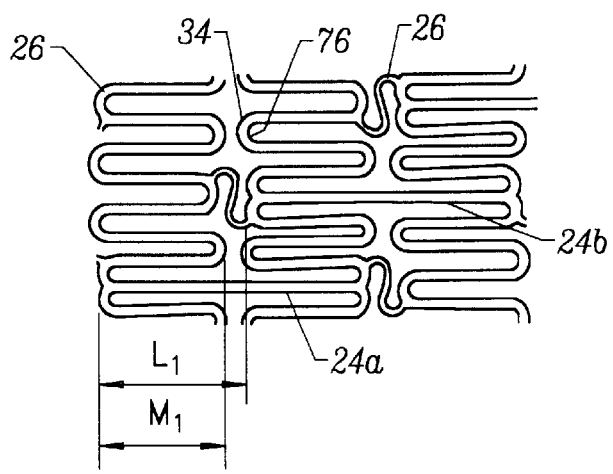
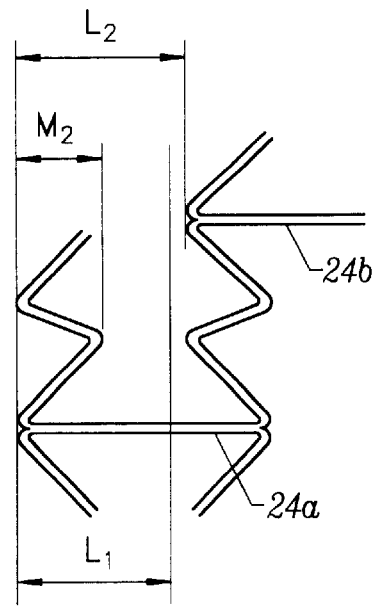
FIG. 8A                FIG. 8B
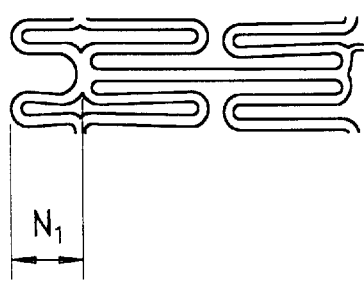
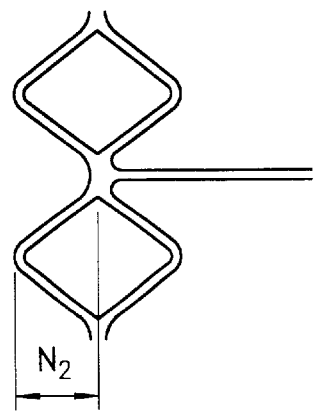
FIG. 8C                FIG. 8D

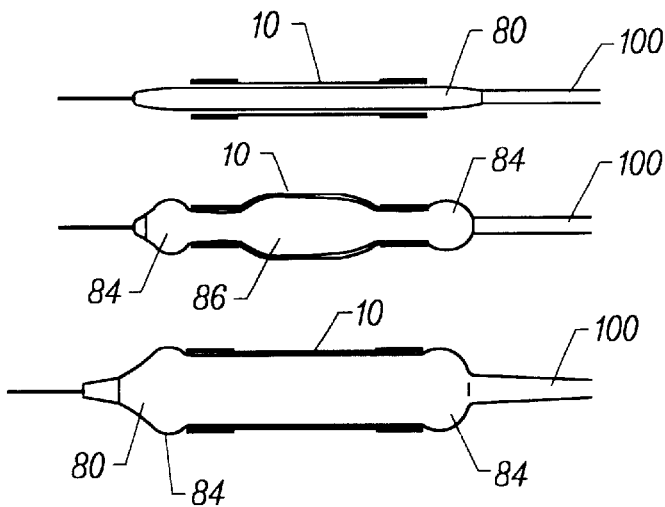
FIG. 16A
FIG. 16B
FIG. 16C
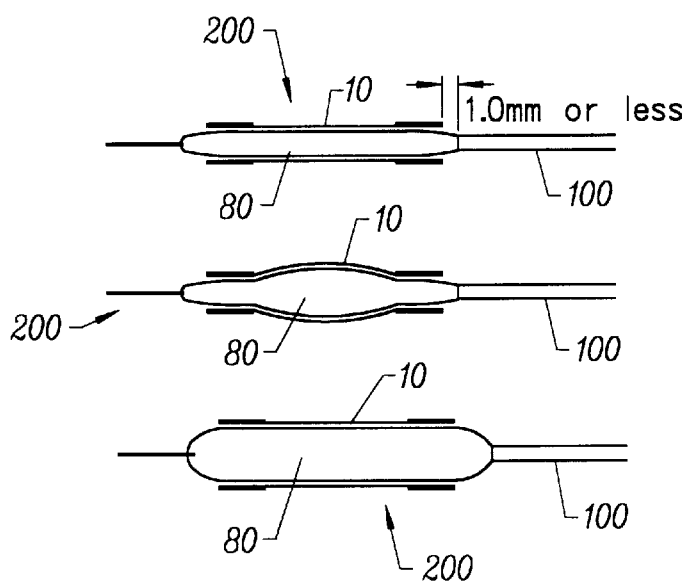
FIG. 17A
FIG. 17B
FIG. 17C

RADIALLY EXPANSIBLE VESSEL SCAFFOLDS MOUNTED OVER BALLOONS

CROSS-REFERENCES TO RELATED APPLICATIONS

This application is a divisional of application Ser. No. 08/968,319, filed on Nov. 12, 1997, which was a continuation-in-part of provisional U.S. patent application Ser. No. 60/060,938, filed on Oct. 23, 1997 and PCT Application Ser. No. PCT/US96/07942 filed on May 29, 1996, which is a continuation-in-part and ciaims priority from U.S. patent application Ser. No. 08/463,166, filed Jun. 5, 1995, now U.S. Pat. No. 5,593,442. The full disclosures of each of these patents and patent applications are incorporated herein by reference.

BACKGROUND OF THE INVENTION

1. Field of the Invention

The present invention relates generally to the structure of radially expansible lumenal prostheses, including stents and grafts. More particularly, the present invention relates to the provision of articulation structures for the construction of flexible and pseudo-flexible prostheses and the provision of end structures for the construction of atraumatically deliverable prostheses.

Lumenal prostheses are provided for a variety of medical purposes. For example, lumenal stents can be placed in various body lumens, such as blood vessels, the ureter, the urethra, biliary tract, and gastrointestinal tract, for maintaining patency. Lumenal stents are particularly useful for placement in pre-dilated atherosclerotic sites in blood vessels. Lumenal grafts can be placed in blood vessels to provide support in diseased regions, such as aortic abdominal, and other aneurysms.

Both stent and graft prostheses must meet certain mechanical criteria to function successfully. In particular, such prostheses should be at least partly flexible or articulated (such as rigid sections that articulate relative to one another) over their lengths so that they may be advanced through tortuous body lumens, such as those of the coronary vasculature. In addition, the prostheses should preferably maintain their original length or foreshorten, minimally when the prostheses assume an expanded configuration. Further such prostheses must have sufficient mechanical strength, particularly hoop strength, in order to mechanically augment the lumenal wall strength and thus assure lumen patency. The ability to meet these requirements is severely limited in the case of cylindrical endolumenal prostheses which are delivered in a radially constrained or collapsed configuration. Such prostheses must radially expand at a target site within the body lumen, so any adaptations which are intended to enhance flexibility will not interfere with the ability to radially expand or to maintain strength once expanded.

Prior lumenal prostheses often have structures which present a risk of injury as they are endolumenally delivered (i.e. tracked) to and/or released at a target site within a patient's body lumen. In particular, many vascular stents comprise a plurality of circumferentially connected and spaced-apart longitudinal elements which deform circumferentially as the stent is radially expanded. The Palmaz stent described in U.S. Pat. Nos. 5,102,417 and 4,776,337, is typical of such stents. When these prostheses are flexed or articulated during delivery or tracking, these longitudinal elements of conventional prosthesis tend to create a phenomenon known as "fishscaling" which occurs when these elements distributed along the length of the prosthesis protrude outward from the surface of the prosthesis. Such stents exhibit poor "tracking"characteristics, where "tracking" is defined as the ability to pass smoothly through tortuous pathways. These protruding elements along the length of the prosthesis increase the likelihood that the prosthesis will dig into or otherwise engage the wall of the body lumen during delivery and even arrest the progress of the prosthesis and its delivery system to the diseased region (or target site). Additionally, a lesser-known phenomenon called "flaring" occurs when the longitudinal elements of the distal or proximal end of the prosthesis are bent outward to assume a crown-like configuration due to bending forces placed on these elements as the prosthesis passes through tortuous body passageways. Flaring can create the same deleterious effects as the previously described fishscaling phenomenon, injuring or traumatizing the blood vessel wall as the prosthesis is delivered or tracked within the blood vessel.

A separate problem in stent construction and deployment relates to the ability to detect the stent fluoroscopically during the deployment procedure. Stainless steel, the most common stent material, is generally radiolucent, i.e. it is minimally visible under x-rays and permits fluoroscopic examination therethrough. Advantageously, such stents do not interfere with subsequent fluoroscopic examination of the treated region of the body lumen, such as six-month-followup examinations. They are, however, much more difficult to accurately position within the lumen due to their radiolucency. To increase radiopacity, these prostheses may be manufactured from radiopaque materials such as tantalum, platinum, or nickel titanium (NiTi). Alternatively, the entire prosthesis may be plated or coated with a uniform layer of radiopaque material to improve prosthesis visualization as disclosed in commonly assigned, co-pending U.S. patent application Ser. No. 08/691,661, filed Aug. 2, 1996, the complete disclosure of which is incorporated herein by reference. Although these methods address the issue of radiopacity, uniform layers of such materials or prostheses made entirely of such materials typically improve radiopacity at the cost of reduced visibility of tissue inside the prosthesis.

For these reasons, it would be desirable to provide improved stents and other lumenal prostheses. In particular, it would be desirable to provide improved lumenal prostheses and methods for their endolumenal placement, where the prostheses can be delivered or tracked to a target site within a body lumen without traumatically engaging the walls of the body lumen. Preferably, the prostheses will have elements which minimize "fishscaling" with its concomitant risk of injury or even retention within the body lumen. Such prostheses may also be provided with minimally traumatic end rings in order to reduce the risk of lumenal injury as the prostheses is both delivered and radially expanded within the body lumen. Optionally, the ends of the prostheses may incorporate stiffening elements which reduce the occurrence of prosthesis flaring or trumpeting during tracking through tortuous body lumens. Additionally, the prostheses will be radially expansible at the target location, and will preferably retain both their cylindrical configuration and flexibility or ability to articulate after expansion. Such prostheses should further have sufficient hoop strength and other mechanical characteristics so that they may effectively function as stents in maintaining lumenal patency and/or grafts in enhancing lumenal wall strength. To more precisely direct scaffolding force at a diseased site, the prosthesis may have specific expanded configurations. Furthermore, it would be desirable to provide improved prostheses having radiopacity characteristics which permit visualization of the prosthesis both during tracking and deployment as well as visualization of tissue within the lumen during subsequent angiographic followup after deployment. The present invention will provide at least some of the desired improvements.

2. Description of the Background Art

Vascular stents comprising multiple segments joined by axial hinge structures are described in U.S. Pat. Nos. 5,195,984; 5,104,404; and 5,102,417 and European Patent Publication EP 540 290. Other stent structures are described in U.S. Pat. No. 5,282,824, European Patent Publication EP 481 365; and Canadian Patent Publication 2,079,944. U.S. Pat. No. 4,776,337 describes the Palmaz stent which consists of multiple longitudinal box elements joined to each other by short circumferentially oriented tabs and usually having at least two such sections joined longitudinally by a single short beam as shown in U.S. Pat. No. 5,195,984.

SUMMARY OF THE INVENTION

The present invention provides improved prostheses and methods for their endolumenal placement within body lumens, particularly blood vessels. The prostheses may be in the form of stents, intended for maintaining lumenal patency, or may be in the form of grafts, intended for protecting or enhancing the strength of the lumenal wall. The prostheses of the present invention will be radially expansible, either by the application of an internal force to expand a minimally resilient (usually malleable) prosthesis structure or by release of radial constraint from a resilient prosthesis structure (self-expanding).

In a first aspect of the present invention, the prosthesis comprises a plurality of radially expansible unit segments, such as rings, having a plurality of beams connecting axially remote points on adjacent unit segments, and a plurality of compliant elements referred to hereinafter as expansion joints connecting axially proximate points on adjacent unit segments. The beams are usually aligned axially and maintain the remote points at a fixed distance at all times including when the prosthesis is radially expanded. The expansion joints, in contrast, allow for relative movement of the proximate points during bending, expansion, or any other deformation of the prosthesis. The expansion joint may have any convenient geometry, such as an "S" shape, a "Z"shape, a serpentine pattern, a zig-zag pattern, or the like. Thus, the expansion joints will provide a compliant, flexible connection of the proximate points on the unit segments to reduce or prevent protrusion or "fishscaling" of these points as the prosthesis is delivered through a tortuous path or deployed (expanded) at a curved target site.

To create the tracking and expansion characteristics desired in the prosthesis, the beams and expansion joints may be positioned in particular patterns between each unit segment. For example, although adjacent unit segments of the prosthesis may be coupled by both expansion joints and beams, they are preferably joined by only one beam and some number of expansion joints. Having only one beam balances the benefits of length compensation and prosthesis flexibility. Beams of the prosthesis are preferably positioned in a "laddered" configuration where the sequence of longitudinal beams is circumferentially and longitudinally staggered, typically with a predetermined amount of longitudinal overlap between the beams when in the unexpanded configuration. The amount of overlap may be about one-third the length of each beam or more preferably one-half the length of each beam. In certain embodiments, beams may also have a weakened midportion of lesser width or lesser thickness than the remainder of the beam to increase transverse flexibility of the prosthesis. The expansion joints may also be weakened to maximize flexibility and minimize interference with the ability of the prosthesis to track. Typically, weakened expansion joints have smaller width or smaller thickness than the longitudinal struts in the unit segments.

In a second aspect of the present invention, the prosthesis may include elements to increase radial stiffness both when unexpanded and when expanded, such as an end segment requiring a greater radial expansion force than another segment in the middle of the prosthesis. In one embodiment, the end segment is a serpentine ring having longitudinal struts of shorter length than the longitudinal struts of segments in the middle of the cylindrical frame. Alternatively, the end rings could have increased stiffness by using hinges of increased width or thickness between each longitudinal portion or strut, as disclosed in commonly assigned, co-pending U.S. patent application Ser. No. 08/691,661, filed Aug. 2, 1996, the complete disclosure of which has been previously incorporated herein. Increased radial stiffiess at the ends of the prosthesis, such as through struts of shorter lengths or box structures with unequal strut lengths, tends to reduce flaring or trumpeting of these ends which may occur during tracking through tortuous passageways. A still further improvement for reducing prosthesis flaring or trumpeting involves using a radially stiffened end segment that is hinged by a long beam to an adjacent segment. The single beam provides articulation between the segments and thus reduces the load placed on the struts in the end segments. Additionally, a prosthesis can be mounted on an inflation member such as a balloon which can shape the expanded prosthesis into a noncylindrical shape. For example, the prosthesis may be expanded into a tapered configuration to provide improved fit and scaffolding in body lumens which have conical configurations. The ability of the inflation member, such as a noncylindrical balloon, to expand a prosthesis into a shape that better conforms to the lumenal geometry may also be enhanced by having unit segments of various radial stiffnesses, such as having a stiffness gradient from one segment to the next, or other nonuniform stifffiesses along the length of the prosthesis.

In a third aspect, a system according to the present invention includes a cylindrical frame forming a prosthesis having a plurality of radially expansible unit segments, a longitudinal length, a distal end and a proximal end. The frame is preferably mounted over an expansible cylindrical section of an inflation member such as a balloon. In this third aspect, the expansible cylindrical section has the same length as the length of the cylindrical frame. Advantageously, this minimizes expansion of the balloon beyond the ends of the prosthesis which may do dissectogenic damage, particularly to the distal the body lumen in which the system is delivered. The inflation section of the balloon is preferably no more than about 1 mm longer from each end of the typically cylindrical frame, more preferably about the same length as the cylindrical frame. The present invention also provides a kit with instructions for use describing a method for mounting a prosthesis over such a matching length balloon together with a mounting tool.

In a fourth aspect, a prosthesis according to the present invention may have a coating of radiopaque material such as gold covering at least the entire outer surface of the prosthesis. The coating will preferably have areas of a first desired thickness and other areas of a second desired thickness. In one embodiment, the ends of the prosthesis have a coating of 0.0006 inches of gold while the remainder of the prosthesis, typically the middle area, has a coating of 0.0003 inches. In another embodiment, a prosthesis may be created using the method of the present invention to create ends having a coating of 0.0006 inches of gold while the middle area has no coating at all. Advantageously, a prosthesis having different thicknesses of radiopaque material added to a radiolucent prosthesis will facilitate the accurate positioning of the prosthesis in the lumen while also allowing for tissue examination following the expansion of the prosthesis and during angiographic followup.

In a further aspect, the present invention provides a method for reinforcing the wall of a body lumen by introducing a prosthesis, having the proximal points of the unit segments constrained by expansion joints and the remote points of adjacent units segments joined preferably by a single beam, to a target site within the body lumen and radially expanding the prosthesis once the target site is reached. The prosthesis may be expanded by applying an expansive force, such as that supplied by a balloon catheter, or alternatively, the prosthesis may be released from a radial constraint at the target site. Alternatively, the method of the present invention may comprise delivering and then expanding a prosthesis having radially constrained or limited ends to reduce the likelihood of prosthesis flaring or trumpeting during delivery or tracking through tortuous body passageways.

A further understanding of the nature and advantages of the invention may be realized by reference to the remaining portions of the specification and the drawings.

BRIEF DESCRIPTION OF THE DRAWINGS

FIG. 3A shows a longitudinal side view of portions of a prosthesis using box structures.

FIG. 3B shows a longitudinal side view of portions of a prosthesis using zig-zag structures.

FIGS. 8A–8D show length compensation effects for beams and box structures used in the present invention.

FIGS. 16A–16C are cross-sectional views of the expansion of a balloon and prosthesis resulting in dissectogenic bulbous ends.

FIGS. 17A–17C are cross-sectional views of the expansion of a length matched balloon and prosthesis of FIGS. 13 and 14.

DESCRIPTION OF THE SPECIFIC EMBODIMENTS

I. Introduction

Figure 1:
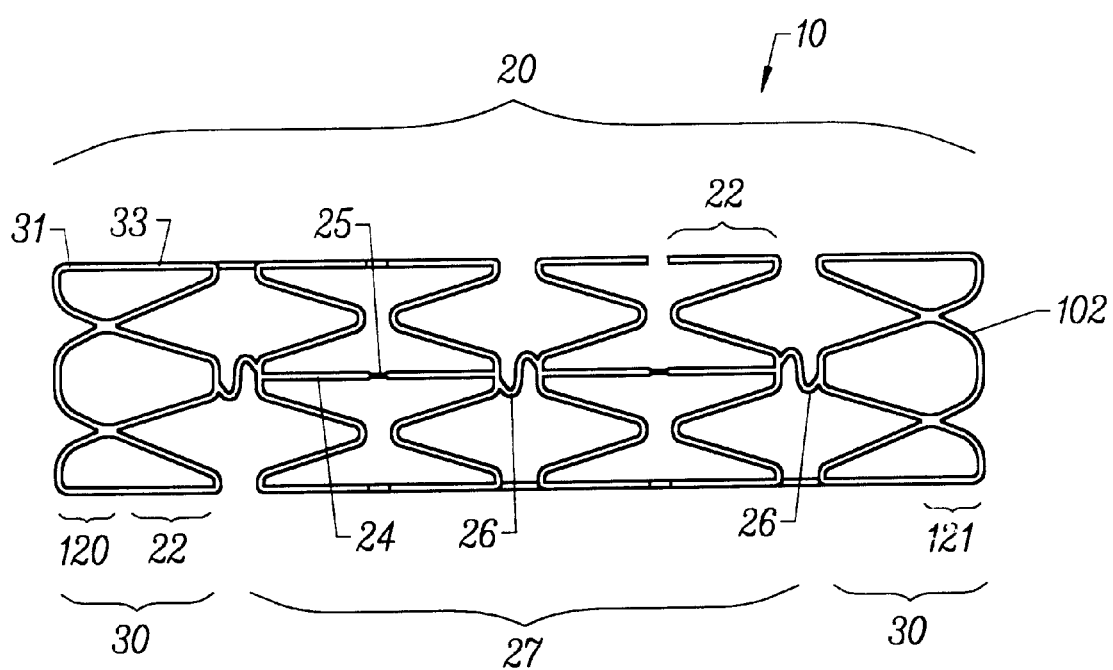
FIG. 1 shows a longitudinal side view of a prosthesis according to the present invention.

The present invention provides devices and methods for the endolumenal placement of prostheses, particularly within the vascular system for the treatment of cardiovascular disease, such as vascular stenoses, dissections, aneurysms, and the like. The apparatus and methods, however, are also useful for placement in other body lumens, such as the ureter, urethra, biliary tract, gastrointestinal tract and the like, for the treatment of other conditions which may benefit from the introduction of a reinforcing or protective structure within the body lumen. The prostheses will be placed endolumenally. As used herein, "endolumenally" will mean placement through a body opening or by percutaneous or cutdown procedures, wherein the prosthesis is translumenally advanced through the body lumen from a remote location to a target site in the lumen. In vascular procedures, the prostheses will typically be introduced "endovascularly" using a catheter over a guidewire under fluoroscopic guidance. The catheters and guidewires may be introduced through conventional access sites to the vascular system, such as through the femoral artery, or brachial, subclavian or radial arteries, for access to the coronary arteries.

A lumenal prosthesis according to the present invention will comprise usually at least two radially expansible, usually cylindrical, body or unit segments. By "radially expansible," it is meant that the segment can be converted from a small diameter configuration (used for endolumenal placement) to a radially expanded, usually cylindrical, configuration which is achieved when the prosthesis is implanted at the desired target site. The prosthesis may be minimally resilient, e.g., malleable, thus requiring the application of an internal force to expand and set it at the target site. Typically, the expansive force can be provided by a balloon, such as the balloon of an angioplasty catheter for vascular procedures. As will be described below, the present invention provides atraumatic connections between successive unit segments which are particularly useful to prevent "fishscaling" in prosthesis which are not protected by sheaths during delivery. Alternatively, the prosthesis can be self-expanding. Such self-expanding structures are provided by utilizing a resilient material, such as a tempered stainless steel or a superelastic alloy such as an NiTi alloy, and forming the body segment so that it possesses its desired, radially-expanded diameter when it is unconstrained, i.e. released from he radially constraining forces of a sheath. In order to remain anchored in the body lumen, the prosthesis will remain partially constrained by the lumen. The self-expanding prosthesis can be tracked and delivered in its radially constrained configuration, e.g. by placing the prosthesis within a delivery sheath or tube and removing the sheath at the target site.

The dimensions of the lumenal prosthesis will depend on its intended use. Typically, the prosthesis will have a length in the range from about 5 mm to 100 mm, usually being from about 8 mm to 50 mm, for vascular applications. The small (radially collapsed) diameter of cylindrical prostheses will usually be in the range from about 1 mm to 10 mm, more usually being in the range from 1.5 mm to 6 mm for vascular applications. The expanded diameter will usually be in the range from about 2 mm to 50 mm, preferably being in the range from about 2.5 mm to 30 mm for vascular applications.

The body or unit segments may be formed from conventional materials used for body lumen stents and grafts, typically being formed from malleable metals, such as 300 series stainless steel, or from resilient metals, such as shape memory alloys, e.g. NiTi alloys, spring steel, and the like. It is possible that the body segments could be formed from combinations of these metals, or combinations of these types of metals and other non-metallic materials. Additional structures for the body or unit segments of the present invention are illustrated in U.S. Pat. Nos. 5,195,417; 5,102,417; and 4,776,337, the full disclosures of which are incorporated herein by reference.

The present invention provides improvements over conventional stents by including both beams and compliant members, preferably nonradially protruding expansion joints, in the design of the prosthesis to minimize longitudinal foreshortening during radial expansion and to maintain a generally smooth outer surface on the prosthesis during delivery. The beams and expansion joints connect together a plurality of unit segments, such as rings with serpentine and/or box structures, and hold the segments at a substantially fixed distance apart from one another. The expansion joints are preferably connected between protruding elements of the unit segments and prevent these protrusions from engaging the wall of the body lumen as the prosthesis is traversed through in the body lumen. The expansion joint is designed to accommodate the flexing of the prosthesis that occurs when tracking the device through tortuous passageways in the body.

The present invention may further include unit segments such as radial rings having increased radial stiffiess on the distal and proximal ends of the prosthesis. Radial expansion as well as compression stiffniess may be increased by shortening the length of longitudinal struts in the ring. These longitudinally shorter unit segments, which may take the form of rings with box structures or serpentine structures, are more resistant to radial expansion than rings having longer struts. Alternatively, segments may be made stiffer by adjusting the hinges connecting the struts together. Whether these stiffer segments are directly connected to the adjacent unit segments or connected by long single beams, these structures minimize flaring or trumpeting of the ends of the prosthesis. Flaring or trumpeting of the prosthesis occurs due to its transverse stiffness which resists the bending and curving of the prosthesis mounted on its delivery catheter during tracking through tortuous pathways. The flaring or trumpeting is undesirable as it will likely cause the prosthesis to engage the body lumen wall and either create trauma to the wall or arrest the delivery of the prosthesis to a target site. Additionally, the prosthesis may be mounted on an expansible inflation member, such as a balloon, having a typically cylindrical inflation section of about the same length as the catheter to reduce especially distal dissectogenic expansion of the balloon. The prosthesis may also be mounted on expansible inflation members with shaped expanded configurations, such a single or multiple taper, to match the prosthesis to the contour of the body lumen or to direct dilatation force of the prosthesis at a target site, such as the ostium of a body lumen.

Still further, the present invention may improve over conventional prostheses by having a coating of radiopaque material having selective thicknesses covering at least parts of the surface of the prosthesis. Advantageously, this allows the radiopacity of the prosthesis to be customized to create, for example, more radiolucent midsections for increased visualization of treated tissue inside the prosthesis while having more radiopaque end sections for facilitating positioning one and juxtaposing/overlapping more than one of the prostheses in a body lumen. These coatings of radiopaque materials may be applied by using selective electroplating or other processes such as dipping or sputtering.

While the prostheses of the present invention will preferably include beams/expansion joints, radially stiffer segments, and selective radiopaque marking schemes as described, it will be appreciated that each of these aspects of the present invention may be employed by itself or in other combinations to provide an improved prosthesis.

II. Embodiments of the Prosthesis

Referring now to FIG. 1, a radially expansible lumenal prosthesis 10 generally comprises a frame 20 formed from a plurality of radially expansible unit segments 22. Although the final shape of the prosthesis 10 will generally be cylindrical, it should be appreciated that the prosthesis may also be conformable to non-cylindrical cross-sectional lumens and may also be conformable to transversely curved lumens. In a first exemplary embodiment of FIG. 2, the frame 20 is formed from a plurality of longitudinally adjacent unit segments 22 connected to one another by a plurality of beams 24 and expansion joints 26. The frame 20 is typically defined as having a midsection 27 which comprises those segments 22 which are not on the longitudinal ends of the frame.

A. Unit Segments

The radially expansible unit segment 22 is the building block from which the frame 20 is forced. Unit segment 22 is preferably formed in the shape of a single, elongate element patterned in a serpentine or "undulating" configuration. It should be noted, however, that a variety of structures incorporating members such as box 30 or zig-zag shapes 32 shown in FIGS. 2, 3A ,and 3B may be used so long as the resulting unit segments 22 are capable of producing the desired radial expansion of lumenal prosthesis 10. Box 30 typically has sets of longitudinal struts 31 and 33 of unequal lengths. The unit segments 22 typically retain a "zig-zag", diamond, or other pattern even after radial expansion to provide adequate support or scaffolding for the vessel wall between consecutive segments and to inhibit localized hyperplasia. Conveniently, the entire prosthesis 10, including the unit segments, beams, and expansion joints can be formed by laser cutting, electric discharge machining, or photochemical etching of thin-wall tubular (i.e. cylindrical) materials. Such techniques are well described in the technical and patent literature.

Radially expansible unit segment 22 is typically characterized as having a plurality of proximate points 34 and remote points 36. The proximate points 34 are defined herein as those locations on the cut surface of the unit segment 22 axially closest to another longitudinally adjacent unit segment 22. These proximate points 34 are typically those locations most likely to engage the wall of a body lumen during tracking or delivery of the prosthesis. The remote points 36 are defined herein, in the broadest definition, as any point spaced apart from a proximate point 34 on the same element of unit segment 22. Remote points 36 on longitudinally adjacent unit segment 22 are generally locations opposed and furthest from each other. The proximate points 34 and remote points 36 are illustrated in FIGS. 2–3B for a variety of segment 22 configurations such as serpentine, zig-zag, and box.

B. Beams and Expansion Joints

Figure 2:
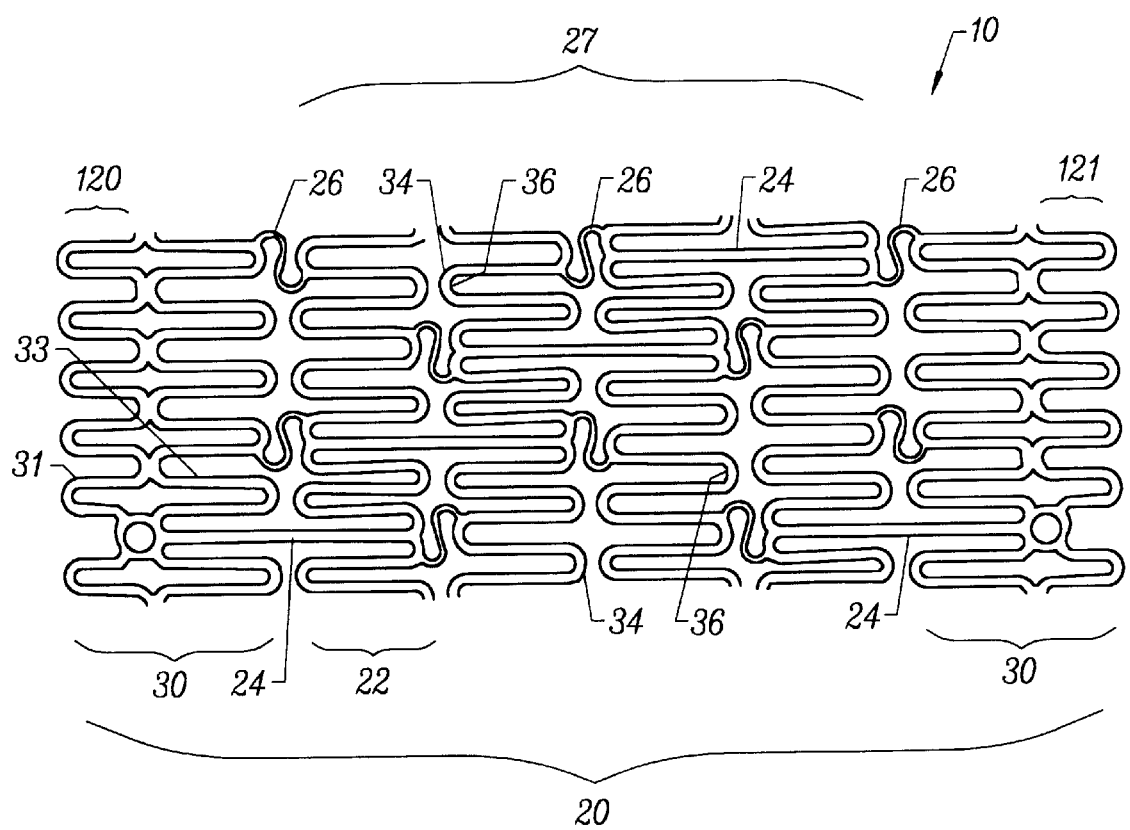
FIG. 2 is a "rolled out" view of a first exemplary embodiment of a prosthesis of the present invention.
Figure 3C:
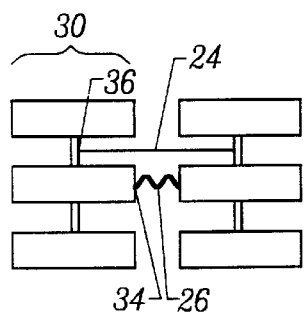
FIG. 3C shows a prior art prosthesis in a curved configuration exhibiting "fishscaling."
Figure 3C:
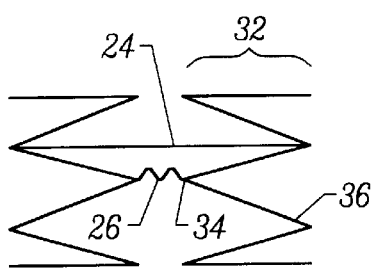
Figure 3C:
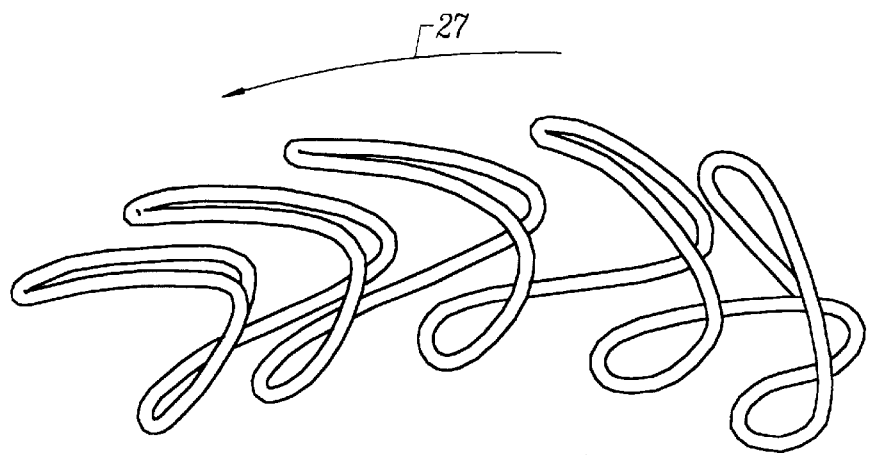
Figure 4A:
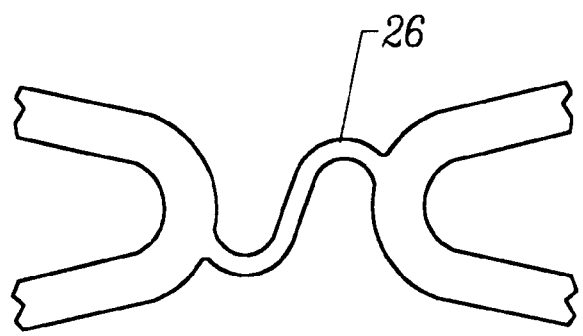
FIGS. 4A–4C show a side view of a expansion joint according to the present invention.
Figure 4B:
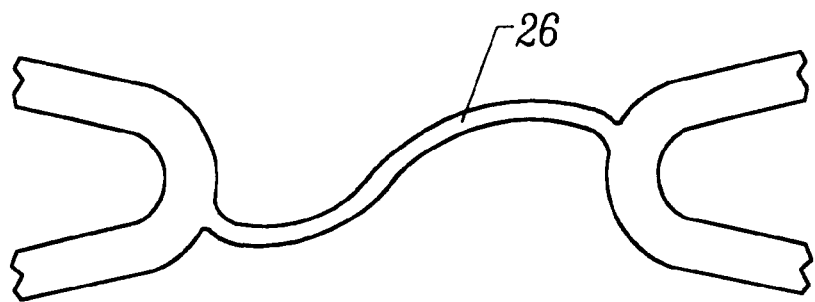
Figure 4C:
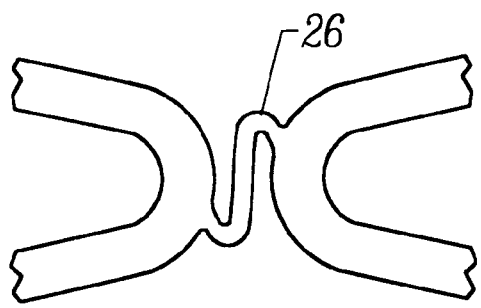

Referring now to FIGS. 1–2, the beams 24 and expansion joints 26 used to couple the unit segments 22 together will now be described. As shown in FIG. 1, the beams 24 are usually straight elongate members in axial alignment with the longitudinal axis of the prosthesis 10. The beams 24 may have a variety of profiles or contours so long as they do not interfere with the function of the prosthesis 10. For example, beams 24 as depicted in FIGS. 1 and 4 have narrowed midportions 25 (narrowing is exaggerated for illustrative purposes) to allow the beams to bend around their midpoints. This enhances longitudinal flexibility and prevents interference between the beam 24 and adjacent struts of segment 22 while the prosthesis flexes during delivery or tracking to the luminal target site. The beams 24 are usually axially aligned, connected to the remote points 36 between unit segments 22, and maintain the remote points 36 at a fixed distance at all times including when the prosthesis 10 is radially expanded.

Figure 3D:
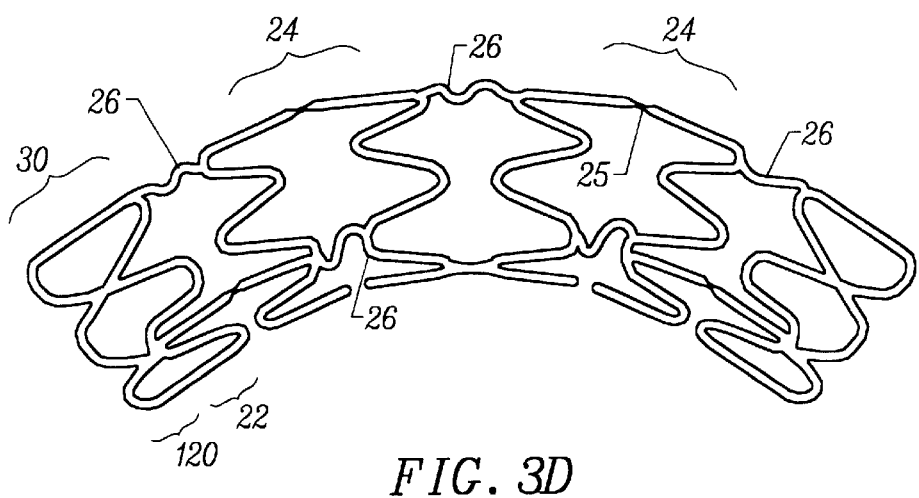
FIG. 3D shows the prosthesis of FIG. 1 in a curved configuration.

Expansion joints 26, which interconnect proximate points 34 between unit segments 22, are used to prevent fishscaling by maintaining a substantially smooth outer surface on the cylindrical frame 20 when the prosthesis 10 assumes a curved configuration. Fishscaling is prominently exhibited by a prior art prosthesis shown in FIG. 3C where the protruding elements of the prior art prosthesis (available as the Freedom stent from Global Therapeutics Inc. of Broomfield, Colorado) can impede the progress or damage the body lumen if the prosthesis is ever retracted or advanced as indicated by arrow 27. The expansion joints 26 of the present invention minimize any detrimental effects from such protrusions. As shown in FIG. 3D, the expansion joints 26 are designed to connect proximate points 34 to maintain a smooth outer surface for the prosthesis 10, while minimally interfering with the relative axial positioning of the unit segments 22. Preferably, the flexibility of prosthesis 10 allows it to remain in this curved configuration without a tendency to straighten, which will unduly strain a curved body lumen and unnecessarily traumatize the lumen at the ends of the prosthesis.

Referring to FIGS. 1–4, the expansion joint 26 may be formed as an "S"shaped member. The "S" configuration allows for axial linear expansion and compression as shown in FIGS. 4A–4C. During this linear expansion and compression, as shown in FIG. 3D, the outer surface remains substantially smooth while the expansion joint 26 is expanded or compressed. When the prosthesis 10 assumes a curved configuration, some of the expansion joints 26 are in compression while others are in expansion, maintaining a smooth outer surface on the frame 20 both on the expanded and the compressed sides of the prosthesis. As shown in FIGS. 1 and 2, not every proximate point 36 is necessarily connected by a expansion joint 26.

Figure 5:
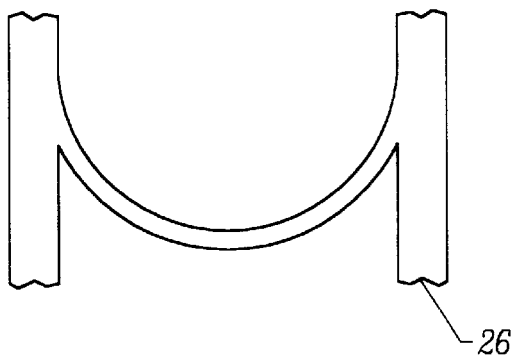
FIGS. 5–7 illustrate a side view of alternative embodiments of a expansion joint of the present invention.
Figure 6:
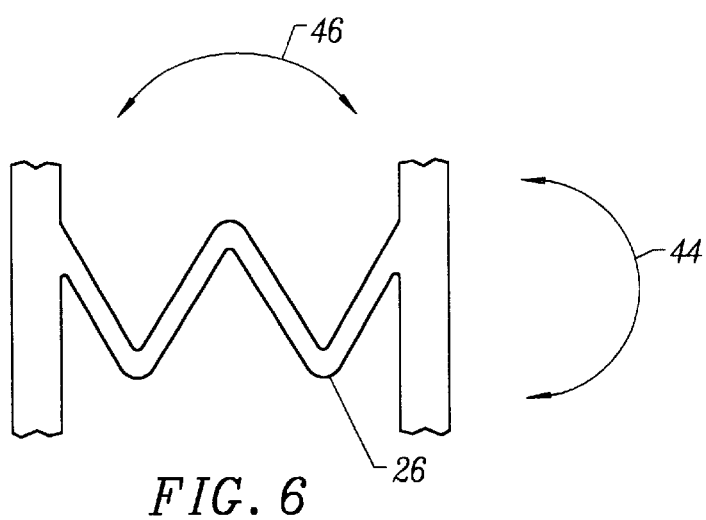
Figure 7:
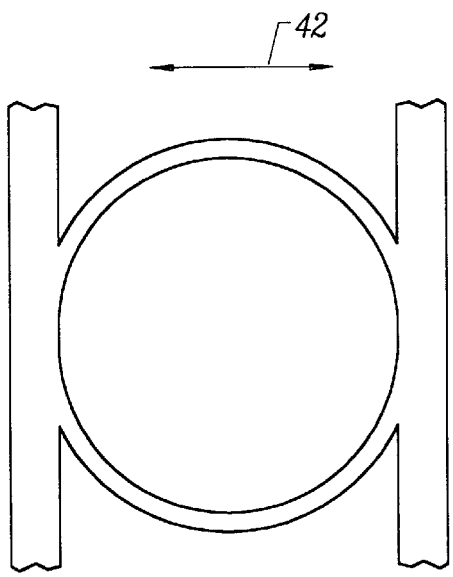

Referring again to FIGS. 4A–4C, the expansion joints are generally made weaker than their adjacent struts to facilitate their plastic deformation. In the example shown, the expansion joints are weakened by having reduced widths. The joints 26 may also be weakened by increasing the length of the joint (when fully extended) or by decreasing the thickness of the joint. As shown in FIGS. 5–7, the expansion joint 26 may assume a variety of other configurations, such as "U"-shaped, "O"-shaped, or zig-zag shaped joints, with the understanding that the joints maintain a substantially smooth outer surface on the prosthesis 10 during delivery. The expansion joint 26 is preferably adapted for axial compression/expansion and transverse flexing, so as to provide the desired linear and flexural degrees of freedom as noted by arrows 42, 44, and 46. The joints 26 are preferably compliant, malleable structures. Though not restricted in this manner, it is desired that the beams are the dominant longitudinal structures and are at most, only minimally inhibited by the joints 26.

C. Pattern

Aside from the flexural characteristics inherent to the beams and joints, the tracking and expansion characteristics of the prosthesis 10 are typically determined by the positions of the beams 24 and expansion joints 26 between the unit segments 22 (FIGS. 1 and 2). For example, a prosthesis 10 using expansion joints 26 will typically have improved tracking capability since the proximal ends are constrained and there is a reduced risk of fishscaling. Likewise, a prosthesis 10 using beams 24 will also have enhanced tracking characteristics by joining adjacent unit segments 22 with a single, long and flexible (malleable) beam providing substantially enhanced articulation between segments during tracking. An important additional advantage of beams 24 relates to improved radial expansion characteristics since prosthesis foreshortening will be substantially compensated by the geometric arrangement of beams and segments. However, having too many beams 24 and joints 26 or too few joints may create other undesirable qualities such as reduced transverse flexibility characteristics of the prosthesis. Hence, there are performance tradeoffs which must be accounted for in the number of and positioning of beams 24 and joints 26 used in the prosthesis 10.

Referring to FIGS. 1 and 2, it should be understood that the beams 24 and expansion joints 26 may be placed in a variety of patterns between the unit segments 22 to balance prosthesis flexibility with competing performance characteristics. In one embodiment shown in FIG. 1, the beams 24 and expansion joints 26 may be linearly aligned in an alternating manner to connect a plurality of adjacent unit segments 22. Adjacent unit segments are connected to one another using only a single beam 24 and one or more expansion joints 26.

FIG. 2 shows a first exemplary embodiment of the prosthesis 10 in a "rolled out" configuration. As shown, adjacent unit segments 22 in FIG. 2 are connected together using both beams 24 and expansion joints 26. As shown in FIG. 2, these beams 24 and expansion joints 26 are not necessarily aligned longitudinally. In this embodiment, only one beam 24 is used per connection between adjacent unit segments 22. This maximizes longitudinal flexibility while providing compensation for longitudinal foreshortening. Further, the beams 24 are in a "laddered" configuration where adjacent beams are laterally (representing the circumferential direction) and longitudinally staggered, with a predetermined amount of longitudinal overlap as shown in FIG. 2 and in a second exemplary embodiment in FIG. 11. The overlap is preferably at least one-third, more preferably about one-half of the length of the beams 24 when the prosthesis 10 is in a collapsed configuration. Advantageously, positioning beams 24 in a laddered configuration results in a spiralling connecting pattern when the prosthesis is seen in its typical cylindrical configuration. This connecting pattern enhances the transverse flexibility of the prosthesis by distributing the single beams around the circumference of the device.

Axial length compensation for the prosthesis, as it is expanded radially from a collapsed to an expanded or deployed configuration, is conveniently achieved by the previously described interconnecting pattern between beams 24 and unit segments 22. The geometrical relationship is best appreciated in FIGS. 8A and 8B which depict three adjacent unit segments 22 both in their collapsed and radially expanded configurations. The axial strut lengths M2 in the expanded configuration are smaller than the axial strut lengths M1 in the collapsed configuration, which is a serious concern in many of the prior art designs. In the present pattern, however, the overall length of the prosthesis, actually grows because the longitudinal distance L2 from the base of a first beam 24a to the base of the next beam 24b is longer than the distance L1 in the collapsed configuration. Furthermore, when the end segments 22 are of the box type as shown in FIGS. 1 and 2, there will be a shortening of the longitudinal length of each box section relative to the base of a first beam 24 as shown in FIGS. 8C and 8D by the difference in the lengths N1 and N2. The lengthening and shortening of the prosthesis described in relation to FIGS. 8A/8B and FIGS. 8C/8D, respectively, can be used advantageously in attaining optimal length compensation when the prosthesis is expanded or deployed.

III. Axially Selective Radial Stiffness

Figure 9:
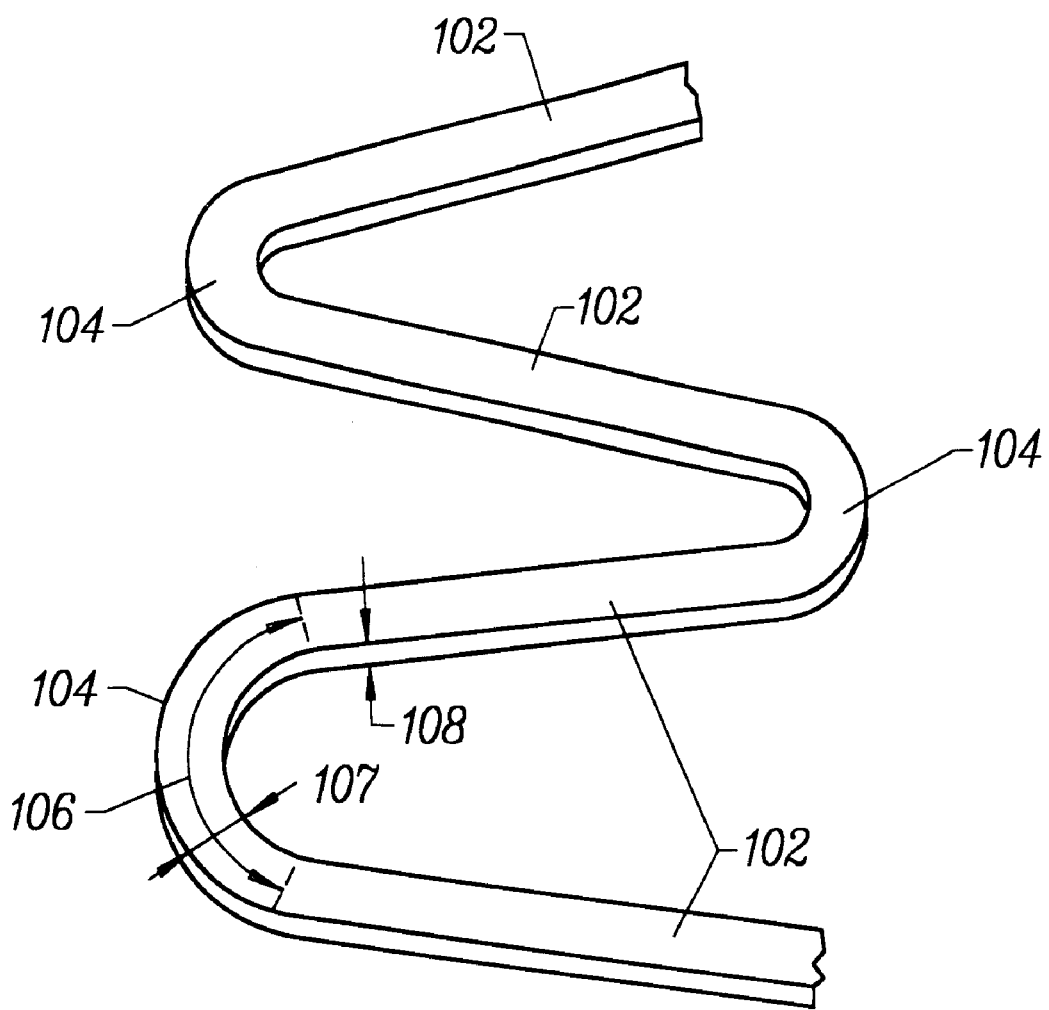
FIG. 9 is a perspective view of a portion of a serpentine ring.

Referring now to FIGS. 9 and 10, a prostheses having axially selective radial stiffnesses can be adapted to control geometrical characteristics resulting in undesired tracking performance. One factor in determining radial stiffness is the type of material used to fabricate the prosthesis. The material is preferably a material such as 316L stainless steel which in its annealed condition is strong yet malleable and will therefore remain in an expanded configuration with a minimum of recoil. Of course, the stronger the material, the harder the prosthesis will be to expand. Another factor in radial stiffness is the length of the struts 102 used in the unit segments 22. The shorter the struts 102, the less leverage or mechanical advantage it will have to deform the hinge element. Therefore shorter struts will require greater forces than longer struts to expand the hinge element between two struts. A further factor involves the design of the hinges 104 connecting adjacent struts 102. The longer, narrower, and thinner the hinge 104 is, as indicated by arrows 106, 107, and 108 respectively, the weaker the hinge will be. The shorter, wider, and thicker the hinge 104 is, the stiffer the hinge 104 will be.

Figure 10A:
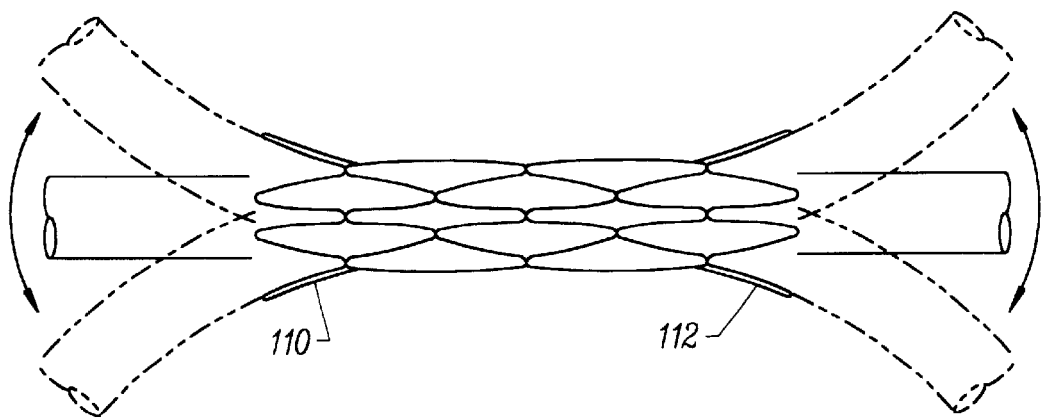
FIG. 10A depicts a prior art stent displaying flared ends due to tracking.
Figure 10B:
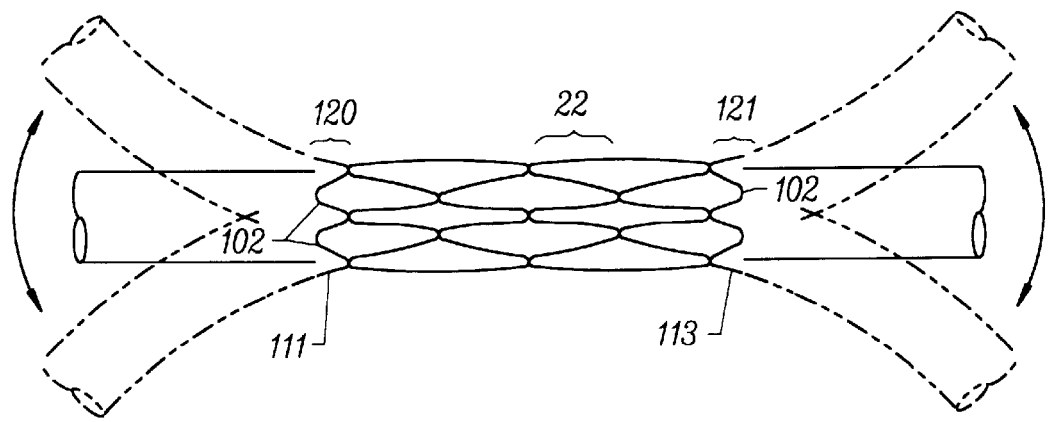
FIG. 10B shows a prosthesis of the present invention having radially stiffer end rings.

Referring to FIGS. 10A and 10B, a prosthesis 10 having axially selective radial expansion stiffnesses will be described. As shown in FIG. 10A, conventional lumenal prostheses have a tendency to flare near the distal end 110 and proximal end 112, especially during tracking through tortuous anatomy, but also when radially expanded by a balloon. This produces an hourglass or double trumpet configuration which may cause trauma to the body lumen wall and even inhibit the progress of the catheter mounted prosthesis during tracking of the prosthesis to the target site. It may also cause excessive end deformation when being expanded, thus potentially being the focus of a stronger restenotic effect. Flaring or trumpeting occurs because the prosthesis resists excessive bending while tracking through tortuous pathways and the struts on the ends of the prosthesis will preferably deform (as illustrated in FIG. 10A), causing the prosthesis to assume a double trumpet shape rather than remaining in the desired cylindrical configuration along its entire length. This occurs particularly in the prior art because the unit segments in the middle of the prosthesis 10 are connected to or constrained by adjacent unit segments and provide transverse rigidity to the prosthesis while those segments on the ends are cantilevered, with only one side constrained. Hence they are more susceptible to deformation during tracking. Because these prosthesis are typically made from malleable materials, they remain deformed even though the delivery catheter may have returned to a straight configuration.

In a preferred embodiment of the prosthesis 10, unit segments near the. vicinity of the distal end 111 and proximal end 113 have a higher radial stiffniess than the unit segments near the center or in the midsection 27 of the prosthesis 10. Although the prosthesis is not limited in this manner, the additional radial stiffniess minimizes the observed flaring. Radial stiffness may be increased in a variety of ways, such as using longitudinally shorter unit segments or by altering the geometry, i.e. widths, lengths, and thicknesses, of the outermost components of the unit segments. The amount of force required to expand the prosthesis may therefore vary over the length of the prosthesis.

In one embodiment as shown in FIG. 10B, end rings 120 and 121 which form the distal end and the proximal end of the prosthesis 10 incorporate a plurality of substantially longitudinal portions or struts 122 which are shorter in length than the longitudinal portions 130 characteristic of the unit segments 22 near the middle of the prosthesis. Although the portions 122 may assume a variety of lengths, the portions are typically half as long as those portions 130 in unit segments 22. These end rings 120 and 121 with the shorter and therefore stronger longitudinal portions will preferably become only minimally flared during the tracking and the expansion of the prosthesis. The end rings 120 and 121 having higher radial stiffniess are preferably included in embodiments of the prosthesis 10, as shown in FIGS. 1 and 2. The end rings 120 and 121 may have a serpentine, zig-zag, or other similar configuration.

Figure 11:
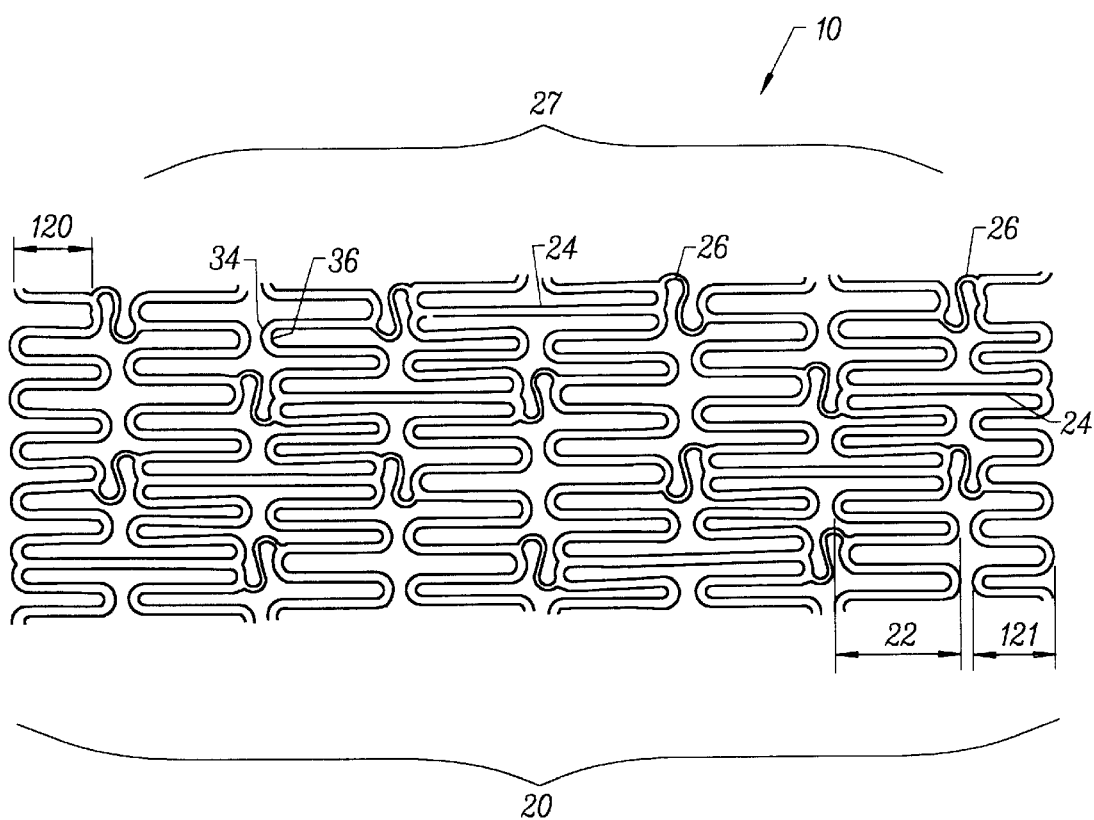
FIG. 11 is a "rolled out" view of a second exemplary embodiment of a prosthesis of the present invention.

In the embodiment of FIG. 11, it is shown that rings 120 and 121 having shorter struts 122 may be coupled to adjacent unit segments by a combination of a single beam 24 and expansion joints 26. One ring 120 or 121 may be directly connected to a unit segment 22, thus forming an articulated structure with the unit segment. Rings 120 or 121 may also be coupled to unit segment 22 by expansion joints 26 to prevent fishscaling without inhibiting transverse flexibility.

In an alternative embodiment, the serpentine ring may incorporate other elements to increase radial stiffness. For example, in FIG. 13, the distal end and proximal end of the prosthesis 10 may be covered by annular sheaths 130 and 131 made of expansible material that radially constrains the ends to minimize flaring and will typically become implanted in body lumen together with the prosthesis. Other suitable devices and methods for constraining the expansion of unit segments 120, 121, and 22, such as expansion limiting hinges, may be found in commonly assigned, co-pending U.S. patent application Ser. No. 08/691,661, filed Aug. 2, 1996, the complete disclosure of which was previously incorporated herein.

IV. Endolumenal Delivery and Expansion

Figure 13:
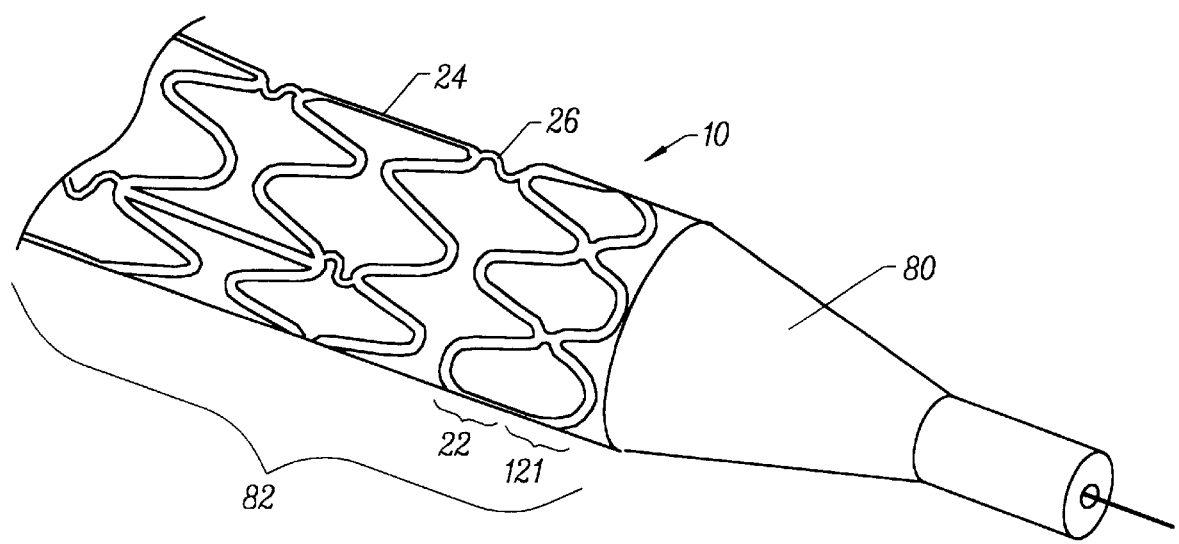
FIG. 13 shows a prosthesis of the present invention mounted on a balloon of a catheter.
Figure 14:
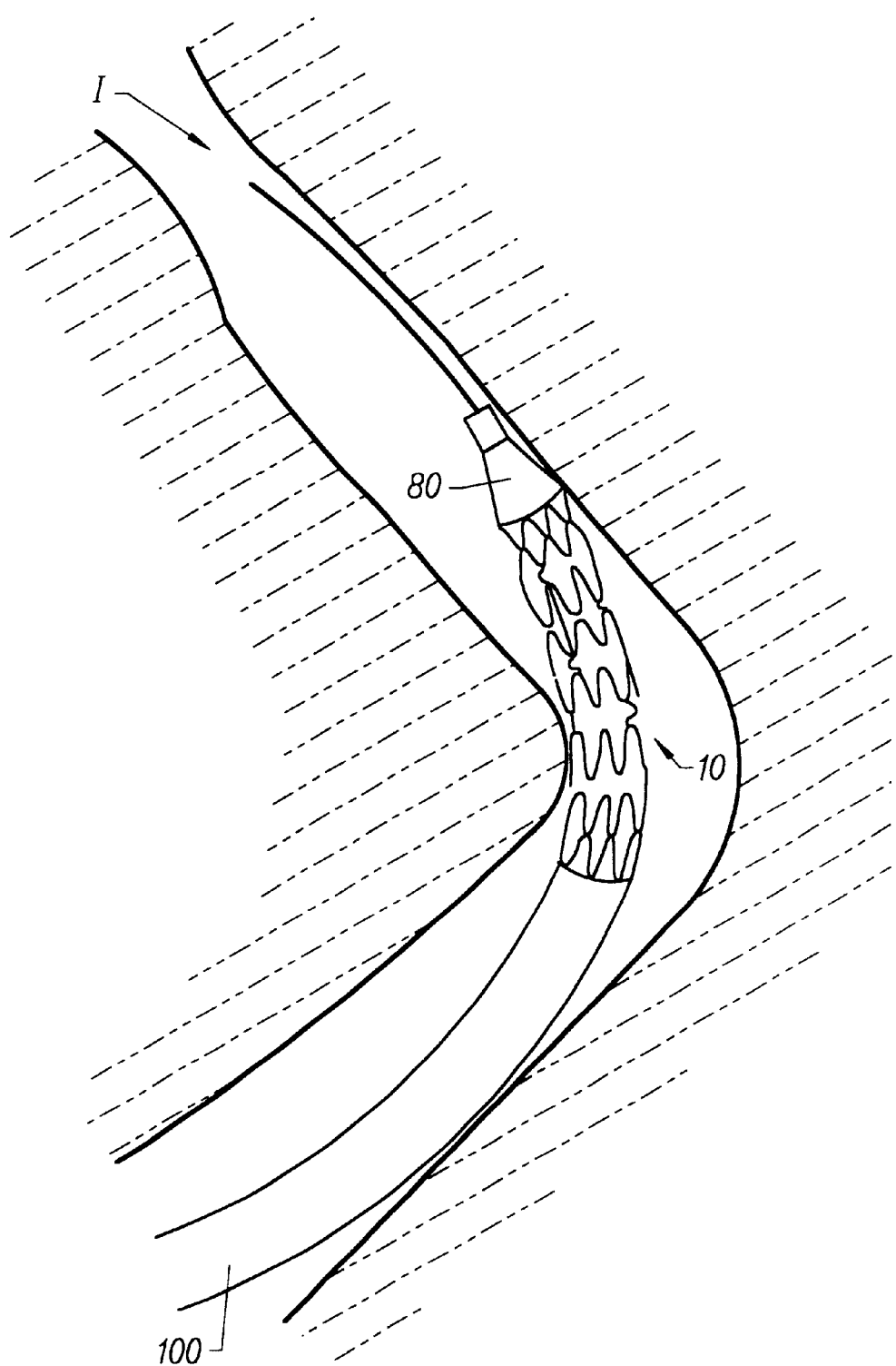
FIG. 14 shows a catheter/prosthesis assembly of FIG. 6 being endovascularly delivered or tracked to a target site in a body lumen.
Figure 15A:
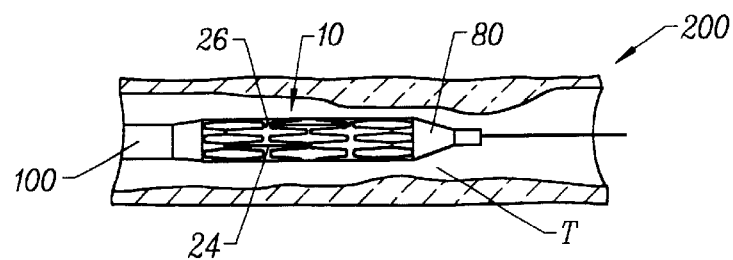
FIGS. 15A–15D shows the catheter/prosthesis system of FIGS. 13 and 14 being delivered, expanded, and secured in a body lumen.
Figure 15B:
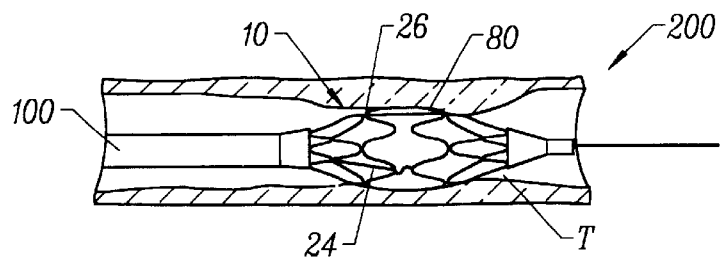
Figure 15C:
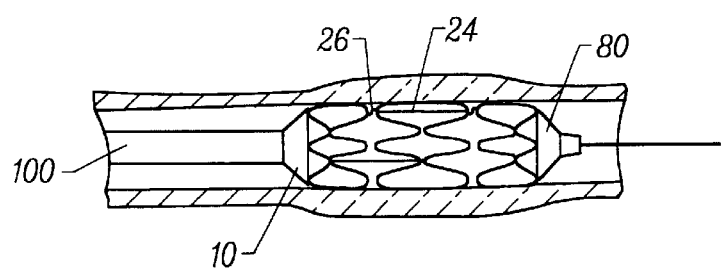
Figure 15D:
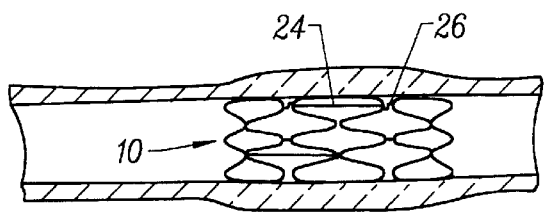

As shown in FIG. 13, in a preferred embodiment, the prosthesis 10 is preferably crimped onto a collapsed expansible inflation member 80 having a typically cylindrical inflation section 82 which is typically located at the distal end of a catheter 100 (FIG. 14). It should be understood, however, that the prosthesis 10 may be coupled to inflation member 80 by other methods known in the art, such as stent delivery sleeves as described in commonly assigned U.S. Pat. No. 5,599,306 or commonly assigned, copending U.S. patent application Ser. No. 08/704,801, filed Aug. 26, 1996, the complete disclosures of which are incorporated herein by reference. In a preferred embodiment, the prosthesis 10 as mounted over an expansible inflation member 80, such as a non-compliant elastomeric balloon, is designed to track through curved and tortuous body lumens as shown in FIG. 14 to reach a target site T. As shown, the expansion joints 26 prevent the prosthesis 10 from engaging the lumen wall when the prosthesis 10 is in a curved configuration. Additionally, the prosthesis 10 preferably includes stiffened radial ends to reduce prosthesis trumpeting. These features improve tracking of the prosthesis 10 through the lumen. When the prosthesis and balloon reach the desired target site T, the expansible member 80 will be expanded to deploy the prosthesis 10 as shown in FIGS. 15A–15D. After the prosthesis 10 has been deployed, the balloon or expansible member 80 will be deflated and removed along with the catheter from the body lumen. The prosthesis 10 will remain in the body lumen to maintain the lumen patency.

In preferred embodiments of the present invention, the prosthesis 10 is mounted on a inflation member 80 of "matching" length to minimize dissectogenic balloon expansion that is characteristic of known catheter/stent assemblies. "Matching" is defined as having an expansible member 80 with an inflation section 82 (cylindrical, tapered, or other shape) of substantially the same length as the length of the prosthesis 10. As can be observed in FIGS. 16A–16C, even when the end sections of the prosthesis are strengthened, the diameter of the outer ends of a conventional balloon 86 exceeds the outer diameter of the prosthesis as the balloon attempts to expand the prosthesis and even following full expansion. The balloon's excessive radial expansion results from inflating portions of the balloon unconstrained by the prosthesis. High pressure inflation (in the range of 10–20 atmospheres) to fully expand the prosthesis into the body lumen may cause these unconstrained portions or bulbs 84 to reach a size sufficient to damage or dissect the body lumen, particularly at the distal end. To eliminate these bulbs 84, a system 200, shown in FIGS. 15A–15D and 17A–17C, according to the present invention preferably uses an expansible inflation member 80 having a cylindrical or other shaped inflation section 82 with approximately the same longitudinal length as that of the prosthesis 10. The "inflation section" may be defined as those areas of the inflation member 80 which can extend beyond the outer diameter of the prosthesis 10 under typical high pressure inflation if unconstrained. Although not limited in this manner, the distal and proximal ends or tips of the member 80 are typically molded and will not expand beyond the diameter of the member. The cylindrical inflation section 82 is no more than about 1.0 mm longer than the prosthesis on each end, preferably no more than about 0.5 mm longer and most preferably the same as the prosthesis. As shown in FIGS. 17A–17C, matching the length of the expanding balloon portion with the length of the prosthesis significantly reduces undesired balloon configurations 84 as the prosthesis 10 is fully expanded in place. It should be understood that the inflation section 82 may assume a variety of configurations once expanded.

Figure 18A:
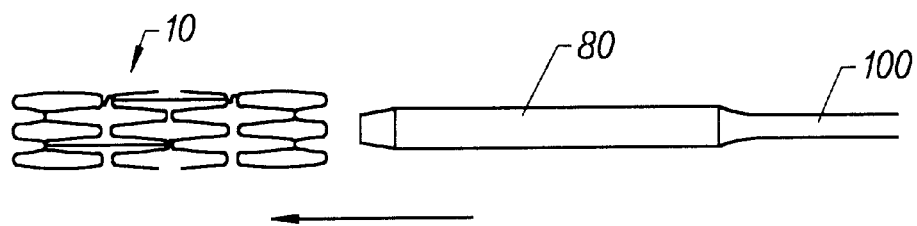
FIGS. 18A–18C illustrate a method for mounting a prosthesis onto an expansible inflation member.
Figure 18B:
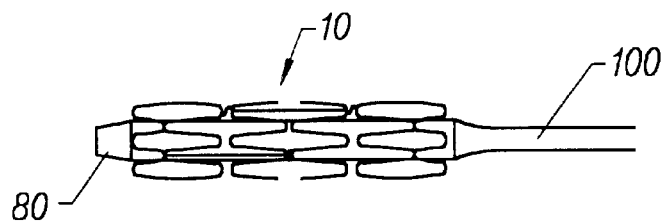
Figure 18C:
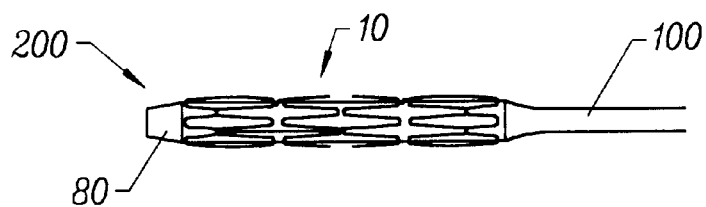

In a preferred embodiment, a system 200 with a prosthesis 10 and expansible member 80 of similar lengths comes with the prosthesis 10 coupled to the expansible member 80. Alternatively, the prosthesis 10 may come as a separate entity that is subsequently mounted onto a suitable expansible inflation member 80. Referring to FIGS. 18A–18C, a method for mounting a prosthesis 10 onto a suitable inflation member 80 includes selecting an expansible inflation member having an inflation section 82 of about the same longitudinal length as the length of a prosthesis 10 (as discussed above). The expansible inflation member 80 is positioned in a longitudinal lumen of said prosthesis 10 prior to the clinical intervention. The position of the longitudinal length of the prosthesis 10 is aligned with the length of the inflation section 82 of the inflation member 80. The prosthesis 10 is then mounted onto the inflation member 80 either by hand crimping or preferably with a crimping tool (not shown). As shown, the inflation member 80 preferably comes with a catheter 100. It is understood, however, that the prosthesis may be premounted at the factory on a delivery device such as a balloon or a sleeve catheter.

Figure 12:
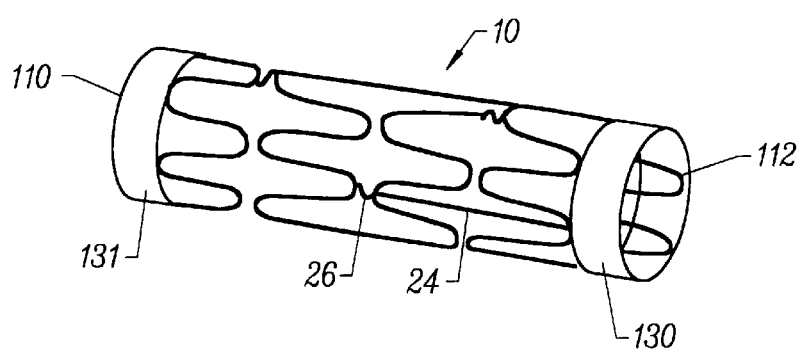
FIG. 12 shows an alternate embodiment of a device for minimizing flaring in a prosthesis.
Figure 19:
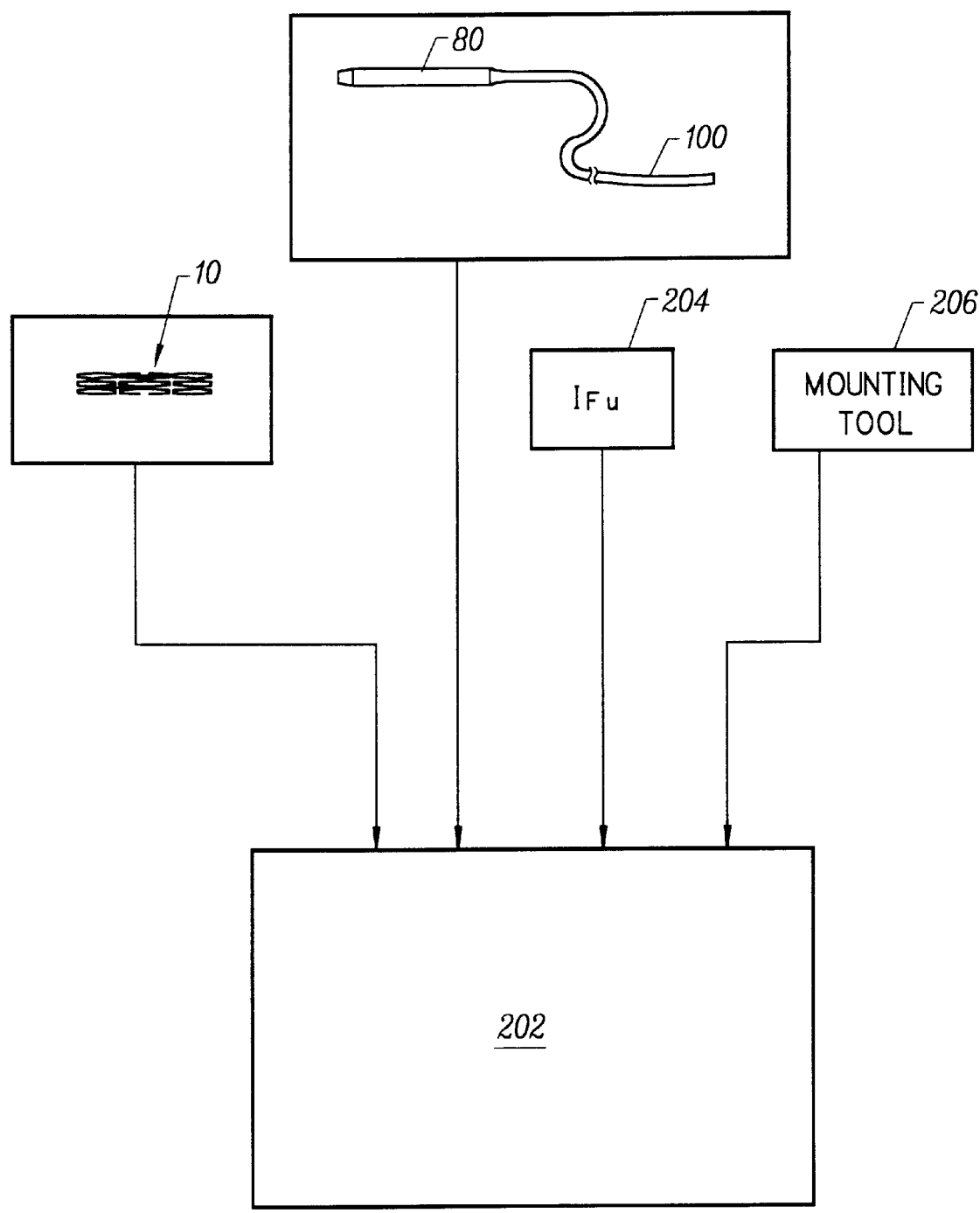
FIG. 19 shows a kit according to the present invention.

Referring to FIG. 19, a prosthesis 10 according to the present invention may be packaged together with instructions for use (IFU) in a kit as shown in FIG. 12. A conventional package, which may be a pouch 202 or any other suitable package, such as a tray, box, tube, or the like, may be used to contain the prosthesis 10 and IFU 204, where the IFU may be printed on a separate sheet and/or may be printed on the packaging itself. The kit may also include a mounting tool 206 such as a crimping device and/or an expansible inflation member 80 which may be permanently or releasably coupled to the prosthesis 10. Typically, the expansible member 80 is attached to catheter 100. The instructions will set forth any of the aspects of the method of the present invention described above, including the method for mounting a prosthesis 10.

Further embodiments of the prosthesis 10 of the present invention may have expanded configurations designed to address specific interventional needs. For example, expanded prostheses configurations may be designed to match the shape of the lumens for which they are targeted. Many body lumens have irregular configurations, and it has been suggested that over 40% of all blood vessels in the body are tapered. To match these body lumen shapes, a prosthesis according to the present invention are preferably be mounted on an expandable balloon 90 which will shape the expanded configuration of the prosthesis as shown in FIGS. 20A–20D respectively. These balloons 90 such as the Banka tapered balloon from C.R. Bard, Inc. of Billerica, Mass. or the CAT balloon from CardioVascular Dynamics, Inc. of Irvine, Calif. may expand into tapered or other desired configurations. A prosthesis of the present invention mounted on such a balloon 90 will have a matching expanded configuration.

Advantageously, matching the prosthesis 10 to the body lumen reduces stress concentrations which may occur when the body lumen is excessively distended by nonconforming (typically cylindrically) expanded prosthesis. A shaped prosthesis further allows for effective scaffolding of lesions having tapered configurations, grant more effective support of lesions at anastomosis sites, and more accurate sizing and scaffolding of ostial lesions. In contrast to conventionally delivered prosthesis, a prosthesis shaped through specific delivery means can concentrate the majority of the supporting force more directly at a lesion site, sparing the surrounding lumenal wall from potentially damaging dilation forces. It should be understood that an unlimited number of results and configurations can be created by varying the radial stiffnesses along the length of the prosthesis and the shape of the delivery system.

Figure 20A:
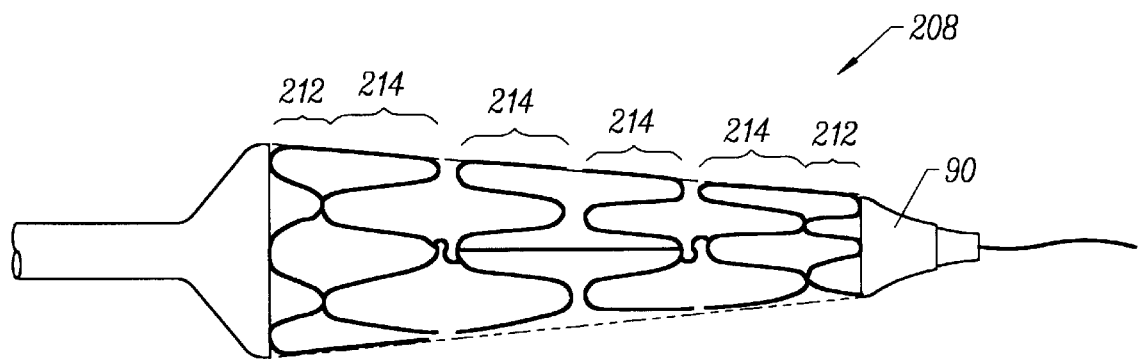
FIGS. 20A–20F show prostheses with various unit segment configurations.
Figure 20B:
Figure 20C:
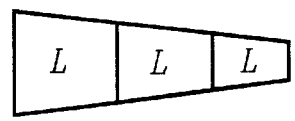
Figure 20D:
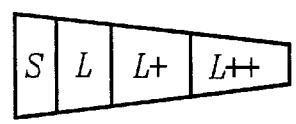
Figure 20E:
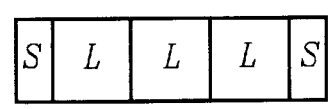
Figure 20F:
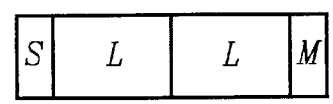

Additionally, as can be seen in FIGS. 20A–20F, the strut lengths can be varied to optimize the dilatation and support forces of the shaped prosthesis. Varying the strut lengths can create a radial stiffness gradient between the unit segments to further enhance lumenal scaffolding. The various prostheses may have struts 212 and 214 with shorter and longer lengths in a tapered expanded configuration (FIG. 20A). Other tapered expanded configurations may have short struts S with long struts L (FIG. 20B), all long struts L (FIG. 20C), or short struts with gradually longer struts L/L+/L++ (FIG. 20D). In cylindrical configurations, the prosthesis 10 may have short struts S and long struts L (FIG. 20E) or short struts S, long struts L, and medium struts M (FIG. 20F). As shown, any combination of strut lengths may be used to optimize desired prosthesis characteristics.

V. Radiopaque Marking Schemes

Proper positioning of a prosthesis in a body lumen can be critical to attain the optimal therapeutic effect from the device. For example, it is sometimes necessary to juxtapose several prostheses in the same body lumen to treat a long lesion. This may require abutting the end of one prosthesis against the end of another prosthesis or slightly overlapping their ends. To visualize the position of these prosthesis as they are delivered into the body lumen, physicians use fluoroscopy or angiography to illuminate the devices in the body lumen. The prostheses preferably have some radiopaque marking features or may be made from radiopaque materials to be detectable by a fluoroscope or similar visualization devices.

Referring to FIGS. 22A–22E, a method for plating a typical prosthesis made from stainless steel with radiopaque material, such as gold, platinum, platinum/iridium, tungsten, tantalum, or the like, will now be described. The method of the present invention creates a prosthesis with a coating of radiopaque material having an axially selective thickness. It should be understood, however, that the method is not limited to thickness variations in the axial direction and may be used to create an unlimited number of thickness configurations. Preferably, the prosthesis is entirely covered with a layer of radiopaque material while having thicker deposits of the same or other materials near its ends and having thinner deposits over the remainder, typically midsection, of the device. When the coating material is gold, the thickness near the ends 111 and 113 is preferably between 0.0003 and 0.0009 inches, more preferably between 0.0004 and 0.0007 inches. Thicknesses over the remainder of the prosthesis may be in the range of 0.0002 to 0.0004 inches. The thicker deposits near the ends of the prosthesis make the ends more radiopaque and thus create a stronger image, facilitating the positioning of the prosthesis in its desired location. The middle area 304 is also preferably coated so as to be more radiopaque than the uncoated material under the fluoroscope, but permitting sufficient radiolucency so that the lumen inside the prosthesis may still be inspected fluoroscopically. Alternatively, the middle area 304 may be left uncoated while only the ends of the prosthesis remain coated to achieve an optimal axial radiopacity distribution. Visualization through this middle area 304 may be crucial for observing future restenotic or hyperplasia within the prosthesis. Coating the entire prosthesis at a uniform thickness using the optimal thickness applied to the ends would likely obscure such visualization. Having an axially selective coating customizes the prosthesis to the desired task. It should be understood that the present method may be used to add materials of a variety of thicknesses to a prosthesis.

Figure 21A:
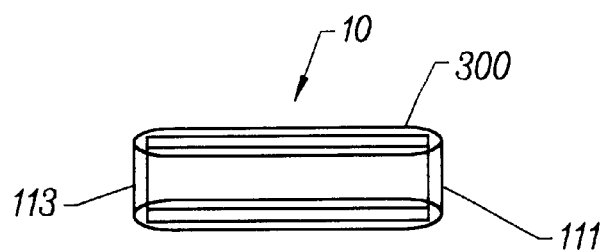
FIGS. 21A–21E depict cross-sectional views of a prosthesis being covered with a layer of radiopaque material having selective thicknesses according to the present invention.
Figure 21B:
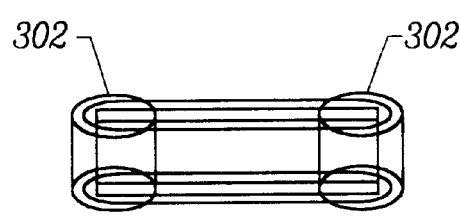
Figure 21C:
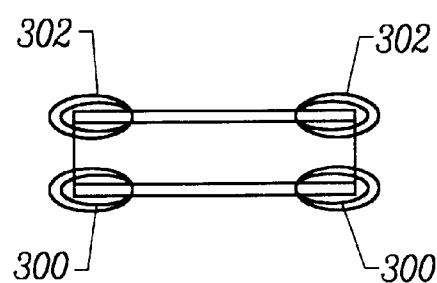
Figure 21D:
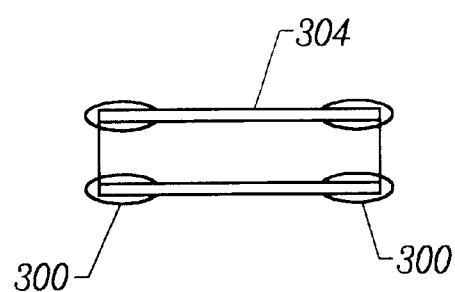
Figure 21E:
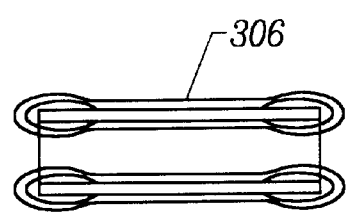

One embodiment of the present method uses electroplating steps to add radiopaque material to the prosthesis. It should be understood, however, that other processes known in the art may also be adapted according to the present invention. The method comprises immersing the completed prosthesis (i.e. cut and polished) in an electrolyte and electroplating the entire prosthesis with a layer 300 of radiopaque material such as gold at a preferred thickness of 0.0003 inches (FIG. 21A). The prosthesis is shown in cross-section, and the plating is shown disproportionately thick for better clarity. The portions of the prosthesis 10 desired to have greater thickness (in this example the two ends) are then covered with a resist material 302 to protect the covered materials from plating removal or plating addition (FIG. 21B). Such resist material 302 may be for example Microposit® FSC® Surface Coating manufactured by the Shipley Company in Marlbourough, Mass. The electroplating process is then reversed to remove radiopaque material not covered with the resist material. In this example of FIG. 21C, it is shown completely removed. The resist material is then removed, leaving behind a prosthesis 10 with select areas covered with a layer 300 of radiopaque material while other areas 304 remain bare (FIG. 21D). The entire prosthesis 10 is then covered with another layer 306 of radiopaque material, such as gold at 0.0003 inches thickness (FIG. 21E). The resulting embodiment of the prosthesis will thus have ends coated with 0.0006 inches of gold, while the remainder of the prosthesis is covered with 0.0003 inches of gold. If a radiopaque coating is desired only at the ends of the prosthesis, the initial coating as shown in FIG. 21A may be made thicker, such as 0.0006 inches of gold, and the final coating step in FIG. 21E may be omitted. This will resulting in a prosthesis having a coating of 0.0006 inches of gold at its ends, and not coating the middle area.

Figure 22A:
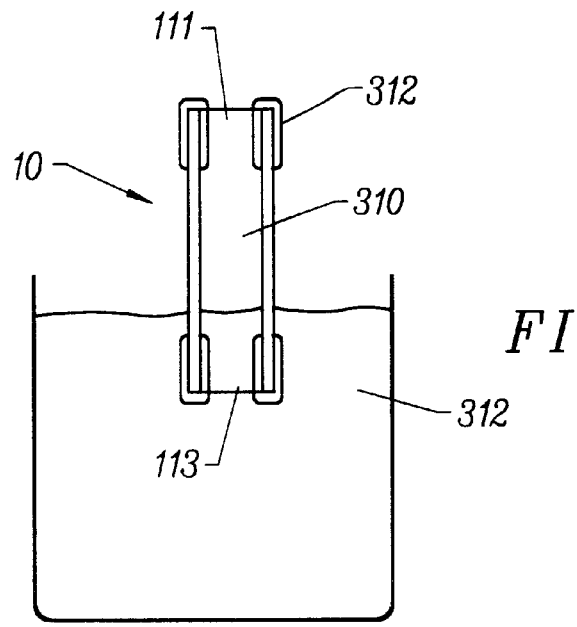
FIGS. 22A–22C show cross-sectional views of a prosthesis being covered by a method for depositing a layer of radiopaque material having selective thicknesses according to the present invention.
Figure 22B:
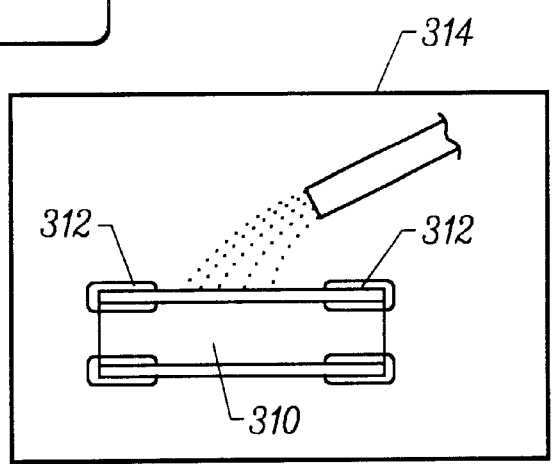
Figure 22C:
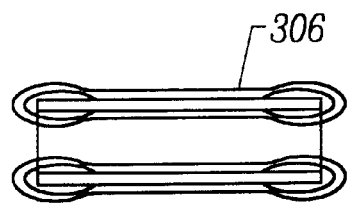

Alternatively, another method for creating selective coatings of radiopaque material may use a combination of electrolytic deposition, electroless dipping, and sputter processes (FIGS. 22A–22C). For example, both ends of the prosthesis are sequentially dipped in radiopaque material, resulting in a prosthesis with a bare middle area 310 and two covered ends 312. This prosthesis can then be entirely recoated using a sputtering process in a vacuum chamber 314 (FIG. 22B). This results in a prosthesis entirely covered with radiopaque material, but having thicker, more opaque ends (FIG. 22C). Although the process using electroplating and the resist material is more flexible as to the shape and location of the areas with thicker coatings, the dipping and/or sputtering processes may also be used to create a prosthesis entirely covered with radiopaque material but having thicker coatings on the ends. It should be understood these method steps may be performed in a variety of different sequences, such as coating the entire prosthesis first and then coating the ends, to create the desired radiopaque coating distribution. Similar thicknesses to gold may be used with other commonly used radiopaque materials such as platinum or platinum/iridium alloys.

Although the foregoing invention has been described in some detail by way of illustration and example, for purposes of clarity of understanding, it will be obvious that certain changes and modifications may be practiced within the scope of the appended claims. For example, the prostheses may be sized as appropriate for use in a variety of body lumens such as the aorta or other vasculature in the body.

What is claimed is:

1. A prosthesis delivery system comprising:

a cylindrical frame formed from a plurality of radially expansible unit segments, said frame having a longitudinal length, a distal end and a proximal end; and a catheter having an expansible balloon having a cylindrical inflation section which prior to expansion has about the same length as the length of the cyindrical frame, wherein the cylindrical frame is mounted over said inflation section of the expansible balloon, and wherein each end of the cylindrical inflation section of the balloon is no more than 1 mm from each adjacent end of the longitudinal length of the cylindrical frame.

2. A system as in claim 1, wherein each end of the cylindrical inflation section of the balloon is no more than 0.5 mm from each adjacent end of the longitudinal length of the cylindrical frame.

3. A method for assembling a prosthesis delivery system comprising the steps of:

providing a radially expansible prosthesis and a catheter having an expansible inflation member with a cylindrical inflation section; and mounting said prosthesis onto the inflation member, wherein each end of the cylindrical inflation section of the inflation member is no more than 1 mm from each adjacent end of the prosthesis prior to expansion.

4. A kit comprising:

a prosthesis for insertion into a body lumen having a longitudinal length and a plurality of radially expansible unit segments;

instructions for use setting forth a method according to claim 4; and a package containing the prosthesis and the instructions for use.

5. A kit of claim 4 further comprising an a catheter having the inflation member.

6. A kit of claim 4 further comprising a crimping tool.

7. A method for assembling a prosthesis delivery system comprising the steps of:

selecting a prosthesis;

selecting a catheter including an expansible inflation member having a cylindrical inflation section of about the same longitudinal length as the length of the prosthesis;

placing the expansible inflation member in a long lumen of sail prosthesis;

aligning the position of the longitudinal length of the prosthesis with the length of the cylindrical inflation section of the expansible inflation member so that each end of the prosthesis is no more than 1 mm from each adjacent end of the longitudinal length of the cylindrical inflation section prior to expansion; and mounting said prosthesis onto the inflation member.

8. A method of claim 7, wherein the mounting step comprises crimping said prosthesis onto the inflation member.

* * * * *